US008280073B2

(12) United States Patent
Ganeshkumar et al.

(10) Patent No.: US 8,280,073 B2
(45) Date of Patent: Oct. 2, 2012

(54) CORRECTING ENGINE NOISE CANCELLATION MICROPHONE DISTURBANCES

(75) Inventors: Alaganandan Ganeshkumar, North Attleboro, MA (US); Davis Y. Pan, Arlington, MA (US)

(73) Assignee: Bose Corporation, Framingham, MA (US)

( * ) Notice: Subject to any disclaimer, the term of this patent is extended or adjusted under 35 U.S.C. 154(b) by 204 days.

(21) Appl. No.: 12/719,268

(22) Filed: Mar. 8, 2010

(65) Prior Publication Data

US 2011/0216917 A1 Sep. 8, 2011

(51) Int. Cl.
*H04B 15/00* (2006.01)
*H04B 1/00* (2006.01)
*A61F 11/06* (2006.01)

(52) U.S. Cl. .................... 381/94.1; 381/94.7; 381/71.11; 381/86

(58) Field of Classification Search ................. 381/94.1, 381/94.7, 86, 71.11, 61, 94.3
See application file for complete search history.

(56) References Cited

U.S. PATENT DOCUMENTS

| | | | | |
|---|---|---|---|---|
| 2,233,459 | A | 3/1941 | Shoup et al. | |
| 3,276,538 | A | 10/1966 | Guyton et al. | |
| 4,085,289 | A | 4/1978 | Schmideler | |
| 4,136,755 | A | 1/1979 | Goes et al. | |
| 4,509,184 | A | 4/1985 | Yanagawa | |
| 4,514,599 | A | 4/1985 | Yanagishima et al. | |
| 5,171,054 | A | 12/1992 | Wilson | |
| 5,193,118 | A | 3/1993 | Latham-Brown et al. | |
| 5,754,665 | A * | 5/1998 | Hosoi | 381/94.1 |
| 6,226,927 | B1 | 5/2001 | Bertolini et al. | |
| 6,882,736 | B2 * | 4/2005 | Dickel et al. | 381/317 |
| 6,937,740 | B2 | 8/2005 | Dage | |
| 6,985,593 | B2 | 1/2006 | Nichols et al. | |
| 7,343,020 | B2 | 3/2008 | Thigpen | |
| 2003/0108210 | A1 | 6/2003 | Dreyer et al. | |
| 2004/0062001 | A1 | 4/2004 | Chang et al. | |
| 2005/0016824 | A1 | 1/2005 | Olcott et al. | |
| 2005/0018868 | A1 | 1/2005 | Chick et al. | |
| 2005/0135642 | A1 | 6/2005 | Dry | |
| 2006/0046780 | A1 | 3/2006 | Subramaniam et al. | |
| 2008/0095383 | A1 | 4/2008 | Pan et al. | |
| 2008/0101645 | A1 | 5/2008 | Rosen | |

FOREIGN PATENT DOCUMENTS

| | | | |
|---|---|---|---|
| DE | 4402412 | A1 | 8/1994 |
| DE | 19654416 | | 5/1998 |
| DE | 19714160 | | 10/1998 |
| DE | 10144786 | | 4/2003 |
| EP | 1475991 | | 11/2004 |
| EP | 1519617 | A2 | 3/2005 |
| EP | 1679936 | A2 | 7/2006 |
| FR | 2780010 | | 12/1999 |
| JP | 5006185 | A | 1/1993 |
| JP | 2001026244 | | 1/2001 |
| WO | 2008051858 | A2 | 5/2008 |

OTHER PUBLICATIONS

International Search Report and Written Opinion dated Jan. 28, 2009, issued in International Application No. PCT/US2007/081972, filed Oct. 19, 2007. International Preliminary Report on Patentability dated Apr. 30, 2009 for PCT/US2007/081972.
International Search Report and Written Opinion for PCT/US2009/057792, dated Dec. 1, 2009.
English abstract of FR 2780010, Dec. 24, 1999, 2 pages.
International Search Report and Written Opinion for PCT/US2011/027009, dated Jul. 5, 2011.

* cited by examiner

*Primary Examiner* — Devona Faulk
*Assistant Examiner* — George Monikang

(57) ABSTRACT

A system for correcting erroneous microphone readings in a vehicle engine harmonic cancellation (EHC) system. A method for operating an engine harmonic cancelling system, includes receiving, from a first microphone at a first location in a vehicle cabin, a signal representative of noise in the vehicle cabin; receiving, from a second microphone at a second location in the vehicle cabin, a signal representative of noise in the vehicle cabin; and correlating the signal from the first microphone with the signal from the second microphone.

13 Claims, 4 Drawing Sheets

CORRECTING ENGINE NOISE CANCELLATION MICROPHONE DISTURBANCES

BACKGROUND

This specification describes an audio system for engine harmonic cancellation (EHC) designed to cancel sinusoidal sounds associated with engine harmonics. An example of an engine harmonic cancellation system is described in U.S. patent application Ser. No. 11/426,537, published as U.S. Pub. 2008/0095383, incorporated herein by reference in its entirety.

SUMMARY

In one aspect, a method for operating an engine harmonic cancelling system, includes: receiving, from a first microphone at a first location in a vehicle cabin, a signal representative of noise in the vehicle cabin; receiving, from a second microphone at a second location in the vehicle cabin, a signal representative of noise in the vehicle cabin; and correlating the signal from the first microphone with the signal from the second microphone. The correlating may include, based on the signal from the first microphone, estimating the signal from the second microphone to provide an estimated second microphone signal; and determining the difference between the estimated second microphone signal and an actual signal from the second microphone. The method may further include comparing the difference with a first threshold. The method may further include determining a ratio between the difference and the estimated second microphone signal and comparing the ratio against a second threshold. The estimating may be done by circuitry that includes an adaptive filter. The method may include comparing the amplitude of the signal from the first microphone and the amplitude of the signal from the second microphone with a threshold, and in the event that the amplitude of the signal from either or both of the first microphone or second microphone is less that a threshold, inhibiting update of the coefficients of the adaptive filter. The method may include determining a ratio of the amplitude of the signal from the first microphone to the amplitude of the signal from the second microphone; and in the event that the ratio of the amplitude of the signal from the first microphone to the amplitude of the signal from the second microphone is greater than a threshold ratio, inhibiting update of the coefficients of the adaptive filter. The method may include smoothing the signal from the first microphone and the signal from the second microphone. The smoothing may include low pass filtering In another aspect, an engine audio harmonic cancellation system includes: at least two microphones and detecting circuitry for detecting the presence of noise that affects the reading of a first of the plurality of microphones differently that the noise affects the reading of a second of the plurality of microphones. The detecting circuitry includes correlation determining circuitry to determine if a signal from the first microphone is correlated with a signal from a second microphone; and comparing circuitry for determining if the amount of noise exceeds a threshold. The correlation determining circuitry may include an adaptive filter, providing, based on the signal from the first microphone, a predicted signal from the second microphone; and the comparing circuitry may compare the predicted signal from the second microphone with the signal from the second microphone. The determining circuitry may include circuitry updating coefficients of the adaptive filter; circuitry comparing the amplitude of the signal from the first microphone and the amplitude of the signal of the second microphone with a threshold; and circuitry inhibiting update of coefficients of the adaptive filter if either or both the amplitude of the signal from the first microphone and the amplitude of the signal from the second microphone are less than the threshold. The determining circuitry may include circuitry updating coefficients of the adaptive filter; circuitry comparing the ratio of the amplitude of the signal from the first microphone to the amplitude of the signal from the second microphone with a threshold; and circuitry inhibiting update of coefficients of the adaptive filter if the ratio of the amplitude of the signal from the first microphone to the amplitude of the signal from the second microphone is greater than the threshold. The engine harmonic cancellation may include smoothing circuitry, smoothing the signal from the first microphone and the signal from the second microphone. The smoothing circuitry may include a low pass filter.

Other features, objects, and advantages will become apparent from the following detailed description, when read in connection with the following drawing, in which:

DETAILED DESCRIPTION

Figure 1:
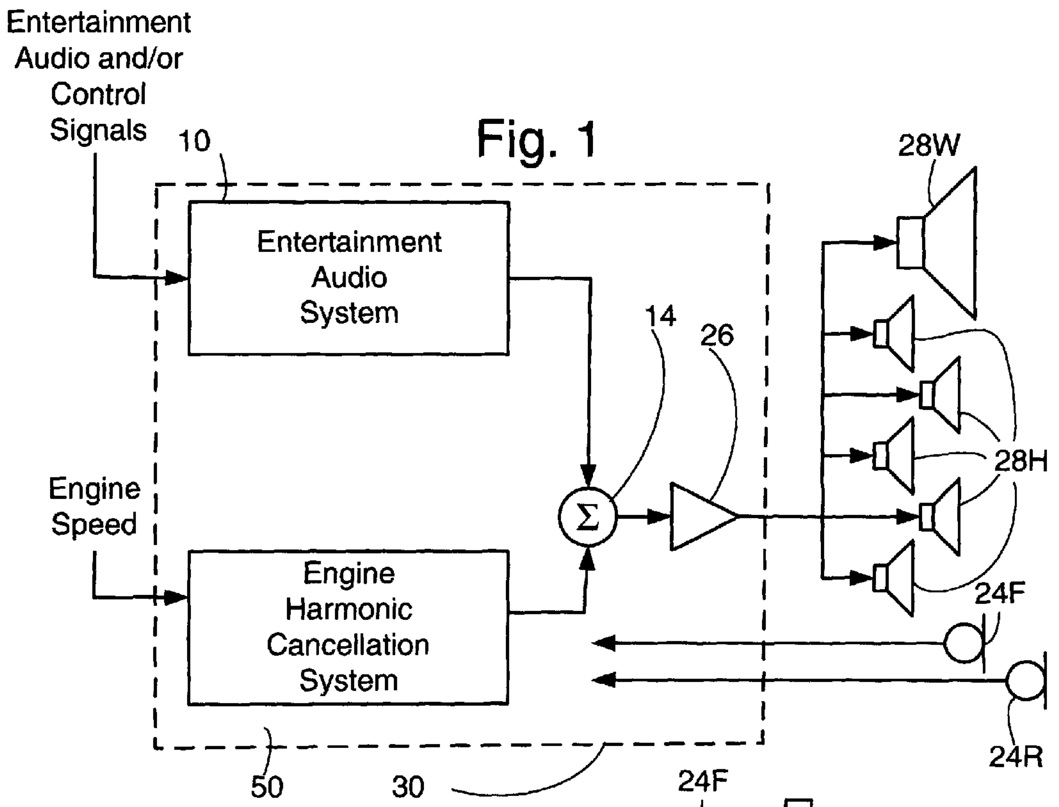
FIG. 1 is a block diagram of an audio system.

Though the elements of several views of the drawing may be shown and described as discrete elements in a block diagram and may be referred to as "circuitry", unless otherwise indicated, the elements may be implemented as one of, or a combination of, analog circuitry, digital circuitry, or one or more microprocessors executing software instructions. The software instructions may include digital signal processing (DSP) instructions. Operations may be performed by analog circuitry or by a microprocessor executing software that performs the mathematical or logical equivalent to the analog operation. Unless otherwise indicated, signal lines may be implemented as discrete analog or digital signal lines, as a single discrete digital signal line with appropriate signal processing to process separate streams of signals, or as elements of a wireless communication system. Some of the processes may be described in block diagrams. The activities that are performed in each block may be performed by one element or by a plurality of elements, and may be separated in time. The elements that perform the activities of a block may be physically separated. Unless otherwise indicated, signals may be encoded and transmitted in either digital or analog form; conventional digital-to-analog or analog-to-digital converters may not be shown in the figures.

FIG. 1 shows some elements of an audio system for a vehicle to provide engine harmonic cancellation. The engine harmonic cancellation (EHC) system 50 accepts as input a reference signal typically indicative of engine speed and signals from one or more microphones 24F and 24R. The engine harmonic cancellation system 50 may be a part of an audio system 30 that includes an entertainment audio system 10. The engine harmonic cancellation system 50 and the entertainment audio system may share some components or may operate through or with common components. For example, noise cancellation signals from the engine harmonic cancellation system and audio signals from the entertainment audio system 10 may be summed at summer 14, amplified by amplifier 26, and transduced to acoustic energy by loudspeakers including woofer 28W and midrange/high frequency loudspeakers 28H.

Figure 2:
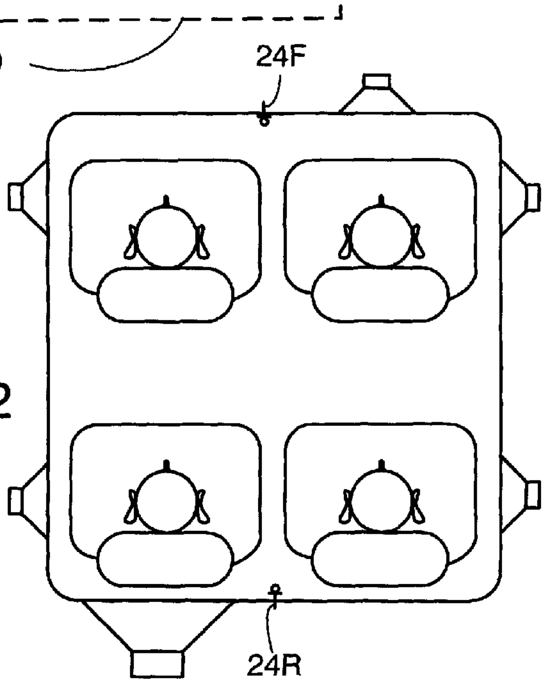
FIG. 2 is a diagrammatic view of a vehicle cabin.

FIG. 2 is a diagrammatic view of a vehicle interior indicating the location of some of the components of FIG. 1. The reference numbers in FIG. 2 refer to elements with like reference numbers of FIG. 1. The microphones may include a front microphone 24F located near the front of the vehicle cabin, for example in the headliner, and a rear microphone 24R, located near the rear of the vehicle cabin, for example also in the headliner. The two microphones 24R and 24F may provide input to the engine harmonic cancellation system 50 of FIG. 1.

In operation, information indicative of the reference frequency is provided to the engine harmonic cancellation system 50. A noise reduction reference signal generator (not shown) generates a noise reduction signal, which may be in the form of a periodic signal, such as a sinusoid having a frequency component related to the engine speed, to an adaptive filter 16. Microphones 24F and 24R detect periodic vibrational energy having a frequency component related to the reference frequency. Based on input from microphones 24R and 24F, the adaptive filter circuitry generates a noise cancellation signal at the reference frequency and harmonics of the reference frequency. The noise cancellation signal may be combined with the audio signal from the entertainment audio system. The noise cancellation signal is amplified by the power amplifier 26 and transduced to vibrational energy by output transducers 28H and 28W. A more complete description of the operation of an EHC system can be found in U.S. Pub. 2005/0095383.

Occasionally, some conditions may cause the microphones to output spurious readings to the engine harmonic cancellation system 50. Some EHC systems have circuitry to ignore or discount some types of spurious readings or cause the EHC system to operate differently than for non-spurious readings. Typical sources of spurious noise include impulse noise such as a vehicle driving over a bump or wind noise resulting from a window being opened. If the engine harmonic cancellation system 50 responds to spurious readings, it may generate a noise cancellation signal based on the spurious readings, which can result in unnatural and unwanted noise audible artifacts. One particularly difficult type of spurious noise is spurious noise that has high amounts of energy in the range of operation of the EHC system and in which the reading from one microphone is substantially different from the other microphone. For example, the vehicle air conditioning and/or heater may have a fan that blows air across a hole in which one of the microphones is located. The airflow may cause a high level of low frequency random noise, which may swamp the harmonic engine noise in the operating frequency range of the engine harmonic cancellation system. In one implementation, the airflow is across a hole in the front headliner garnish, so the examples that follow assume that the front microphone is affected by the airflow. In other implementations, it may be the rear microphone that is affected by the airflow, in which case “front” and “rear” would be reversed.

Figure 3:
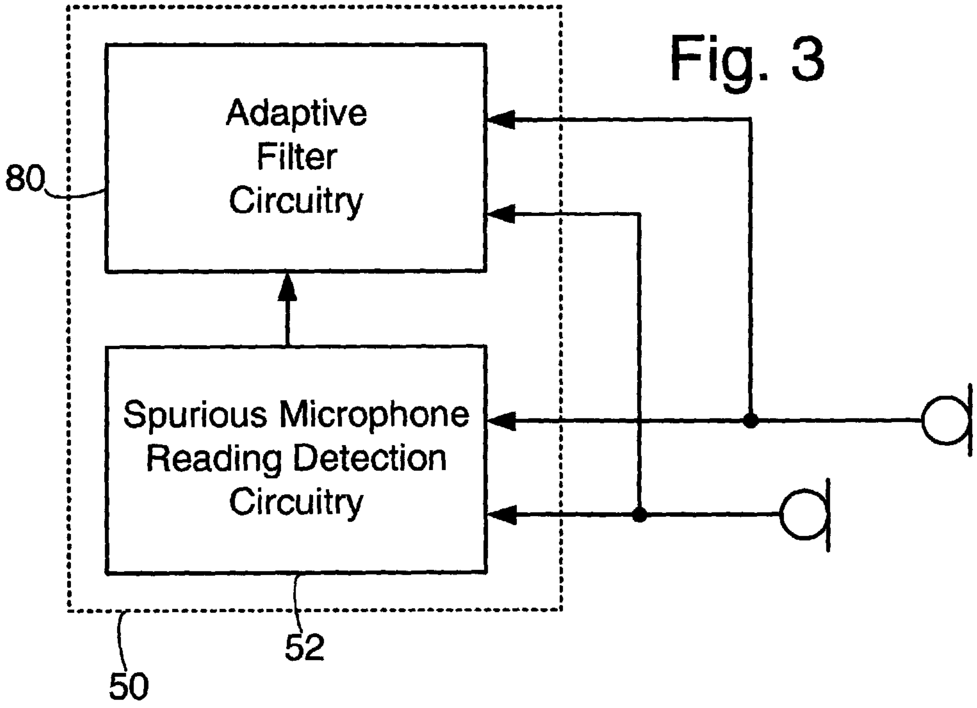
FIG. 3 is a block diagram of a portion of an engine harmonic cancellation (EHC) system.

FIG. 3 shows some additional components of the engine harmonic cancellation system 50. In addition to the adaptive filter circuitry 80, the engine harmonic cancellation system may include circuitry for detecting microphone readings resulting from spurious noise that has high amounts of energy in the range of operation of the EHC system and in which the reading from one microphone is substantially different from the other microphone (hereinafter spurious microphone reading detection circuitry 52). The spurious microphone reading detection circuitry 52 may accept input from the microphones 24R and 24F and examines the input to determine if the input from the microphones is spurious and if the spurious noise is excessive.

Figure 4:
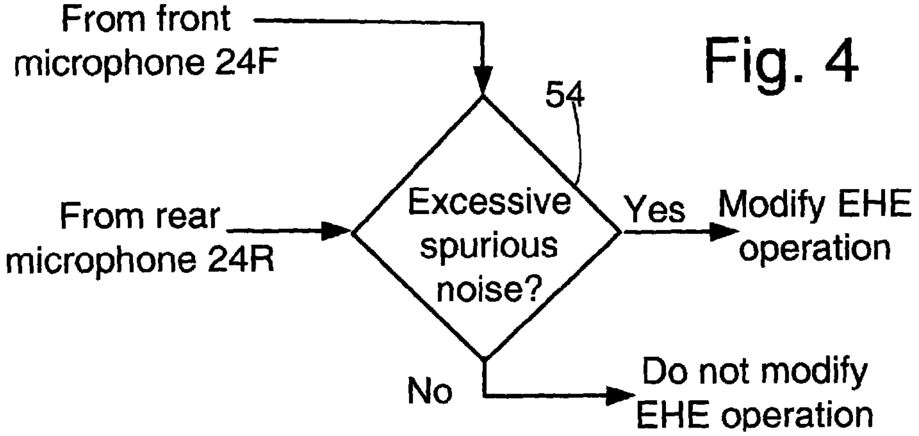
FIGS. 4 and 5 are block diagrams illustrating the operation of a portion of EHC system.

As shown in FIG. 4, if it is determined at block 54 that the input from one or more of the microphones is spurious, and if the spurious noise is excessive, the operation of the EHC system may be modified. Modifying the operation of the EHC system may take a number of forms. If it can be determined from which microphone the spurious noise comes, that microphone may be ignored until the spurious noise ceases. If the EHC system includes an adaptive filter, the filter may be turned off; the leakage factor may be modified, as described in U.S. Pub. 2005/0095383; parameters of the adaptive filter may be changed; or other modifications to the operation of the adaptive filter may be made.

Figure 5:
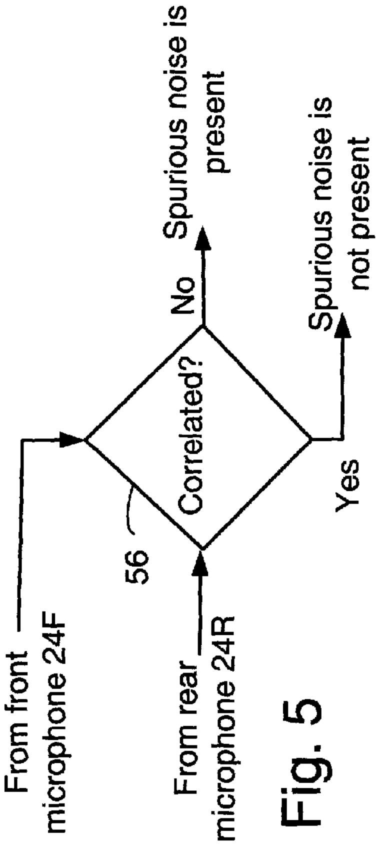

FIG. 5 shows one method of determining if there is spurious noise. Generally, road noise and noise from the sources related to engine noise (which the EHC system is designed to attenuate) is correlated between the microphones, and spurious noise is not correlated. Thus, at block 56, it is determined if the readings from the two microphones are correlated, then it is determined that there is no spurious noise. If it is determined at block 56 that the readings from the two microphones are not correlated, it is determined that there is spurious noise.

Figure 6:
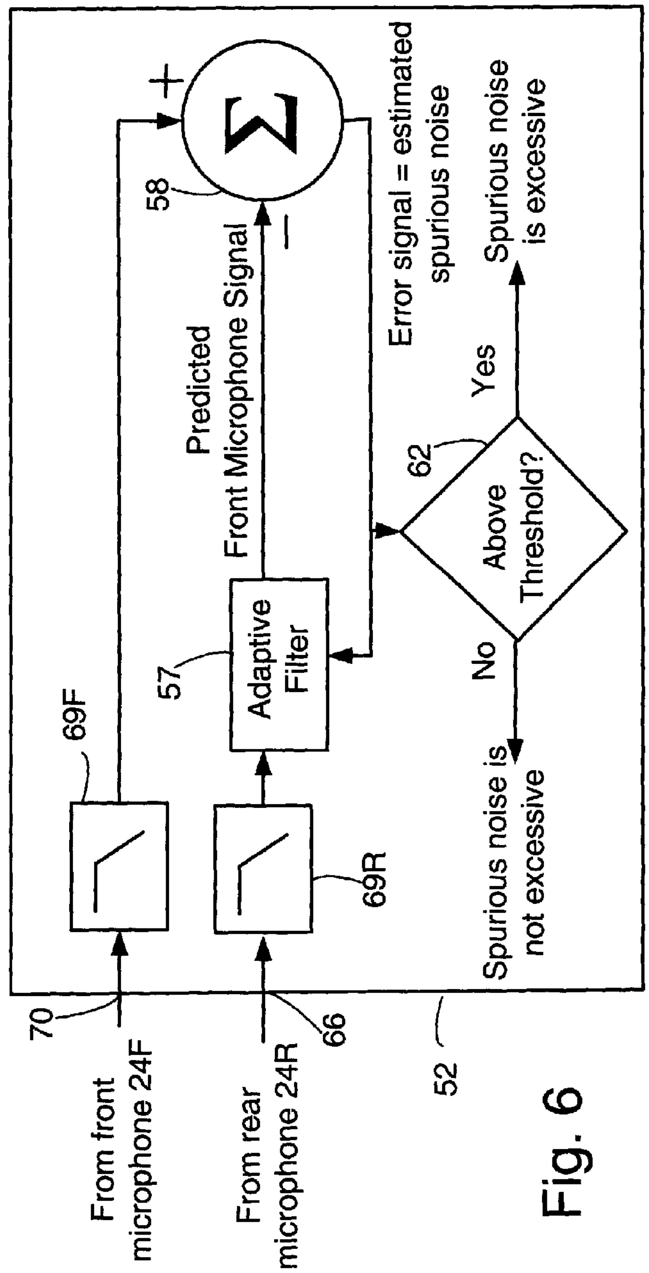
FIGS. 6 and 7 are block diagrams of implementations of portions of an EHC system.

FIG. 6 shows spurious microphone reading detection circuitry 52 that determines if the spurious noise is present and if present, if it is excessive. In the spurious microphone reading detection circuitry 52 of FIG. 6, the input 66 for the signal from the rear microphone 24R is coupled to an adaptive filter 57, which is subtractively coupled to summer 58. In some implementations, input 66 may be coupled to the adaptive filter 57 by a low pass filter 69R. The input 70 for the signal from the front microphone 24F is coupled to summer 58, in some implementations through a low pass filter 69F. The output of summer 58 is coupled to adaptive filter 57 and to threshold comparison block 62. In one implementation, the break frequencies of the low pass filters 69F and 69R is 10 Hz, which is below the range of entertainment audio signals.

Typically, the readings from the two microphones are correlated. In the spurious microphone reading detection circuitry 52 of FIG. 6, the reading from one of the microphones, in this example, the rear microphone 24R, is input to adaptive filter 57. The adaptive filter 57 predicts the reading from the other microphone, in this example, the front microphone 24F. The predicted reading is combined subtractively at summer 58 with the actual reading of the other microphone to develop an error signal representing the difference between the actual reading of the front microphone and the predicted reading of the front microphone. The difference represents the spurious noise. The amplitude of the error signal is compared to a threshold at block 62. If amplitude of the error signal exceeds the threshold, it is determined that the spurious noise is excessive. If the amplitude of the error signal does not exceed the threshold, it is determined that the spurious noise is not excessive.

The error signal of FIG. 6 may be used in a conventional manner, to update the coefficients of the adaptive filter 57. However in some situations, it may be desirable to inhibit adaptation (that is, updating of the filter coefficients) of the adaptive filter 57. For example, if the amplitude of the signal from either of the microphones 24F, 24R, is below a threshold, for example, 40 dB spl, adaptation may be inhibited; or if the ratio between the signal from one of the microphones 24F or 24R and the signal from the other microphone is greater than a threshold, for example 12 dB, adaptation may be inhibited. If adaptation is inhibited, the comparison at block 62 between the error signal and the threshold is performed with adaptive filter coefficients that are not updated.

The spurious microphone reading detection circuitry 52 works effectively if the threshold can be set high enough to prevent false findings of excessive spurious noise. Sometimes at low levels of engine noise, a high threshold may result in findings that spurious noise is not excessive when there is sufficient spurious noise to result in audible artifacts.

Figure 7:
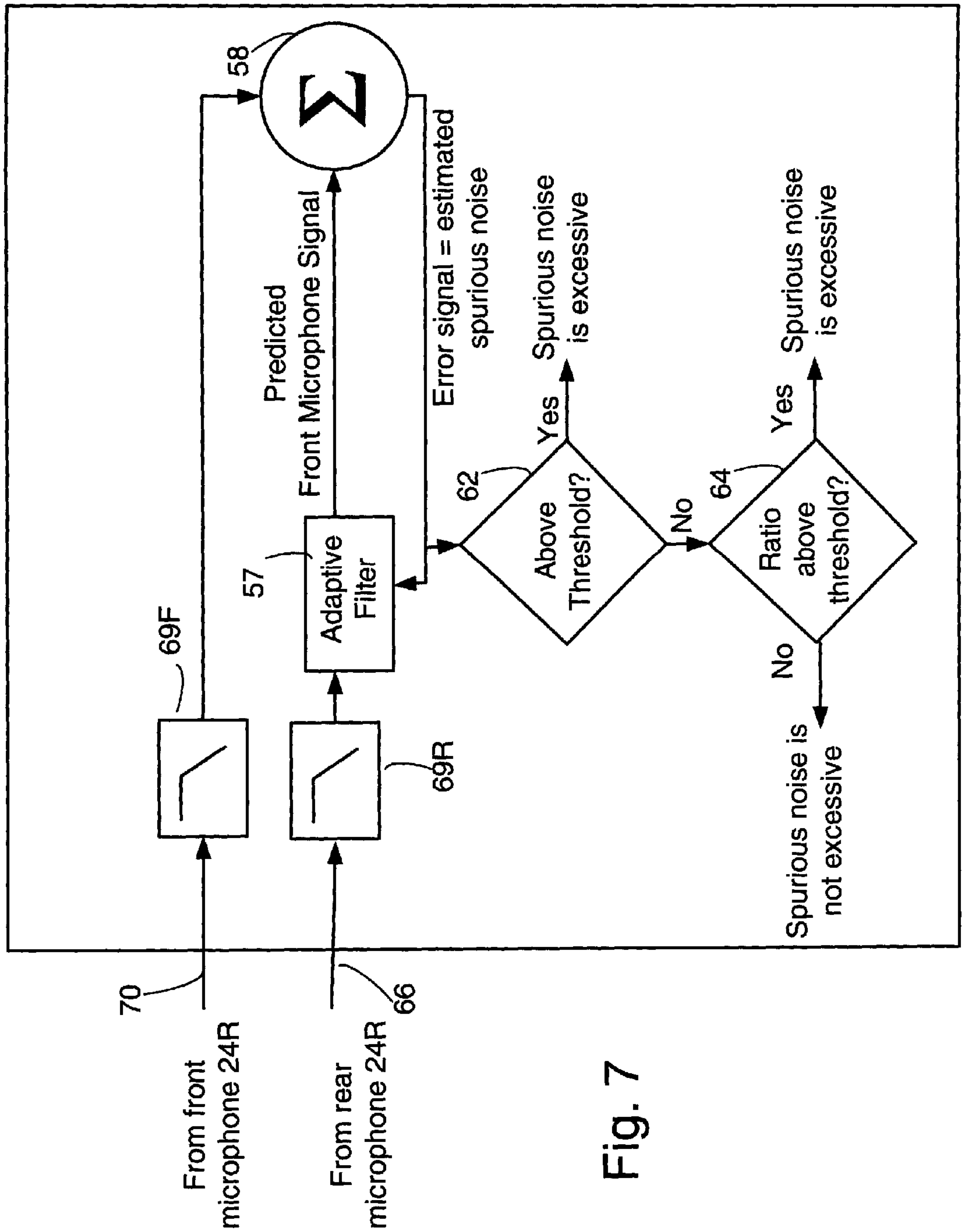

FIG. 7 shows spurious microphone reading detection circuitry 52 that has additional features to provide accurate readings at low levels of road noise. In addition to the components of the spurious microphone reading detection circuitry 52 of FIG. 6, the spurious microphone reading detection circuitry 52 includes a second comparison block 64 that operates if the result of comparison block 62 is NO. In operation, the spurious microphone reading detection circuitry 52 calculates a spurious noise to road noise ratio:

$$\text{ratio} = \frac{\text{front\_mic\_reading} - \text{predicted\_front\_mic\_reading}}{\text{predicted\_front\_mic\_reading} + \text{offset}}$$

in which front_mic_reading is the actual front microphone reading and predicted_front_mic_reading is the front mic reading predicted by the adaptive filter based on the rear microphone reading. The numerator represents the spurious noise. The denominator represents the noise that would be present if the rear mic reading is predictive of the front microphone, or in other words, the road noise that would be present if the reading of the front mic were not subject to the spurious noise. The ratio can then be compared to a ratio threshold.

Even if the amount of spurious noise is small, if the amount of road noise is small, the ratio can still be large. If the amount of road noise approaches zero, then the numerator of the ratio approaches the spurious noise and the denominator approaches the offset. As the level of road noise increases, the denominator becomes larger, and the ratio may not exceed the threshold even in the presence of spurious noise. However, at high levels of road noise, the comparison at block 62 is unlikely to find that spurious noise is not excessive when there is sufficient spurious noise to result in audible artifacts.

Similar to the operation of the spurious microphone reading detection circuitry of FIG. 6, the error signal of FIG. 7 may be used in a conventional manner, to update the coefficients of the adaptive filter 57. However in some situations, it may be desirable to inhibit adaptation (that is, updating of the filter coefficients) of the adaptive filter 57. For example, if the amplitude of the signal from either of the microphones 24F, 24R, is below a threshold, for example, 40 dB spl, adaptation may be inhibited; or if the ratio between the signal from one of the microphones 24F or 24R and the signal from the other microphone is greater than a threshold, for example 12 dB, adaptation may be inhibited. If adaptation is inhibited, the comparison at block 62 between the error signal and the threshold is performed with adaptive filter coefficients that are not updated.

A method using correlation is advantageous over methods that directly compare the signal from the front microphone with the signal from a second microphone because methods using correlation are less susceptible to tolerance differences in the microphones.

Numerous uses of and departures from the specific apparatus and techniques disclosed herein may be made without departing from the inventive concepts. Consequently, the invention is to be construed as embracing each and every novel feature and novel combination of features disclosed herein and limited only by the spirit and scope of the appended claims.

What is claimed is:

1. A method for operating an engine harmonic cancelling system, comprising:

receiving, from a first microphone at a first location in a vehicle cabin, a signal representative of noise in the vehicle cabin;

receiving, from a second microphone at a second location in the vehicle cabin, a signal representative of noise in the vehicle cabin; and correlating the signal from the first microphone with the signal from the second microphone, wherein the correlating comprises:

based on the signal from the first microphone, estimating the signal from the second microphone to provide an estimated second microphone signal; and determining the difference between the estimated second microphone signal and an actual signal from the second microphone.

2. A method according to claim 1, further comprising comparing the difference with a first threshold.

3. A method according to claim 2, further comprising determining a ratio between the difference and the estimated second microphone signal; and comparing the ratio against a second threshold.

4. A method according to claim 1, wherein the estimating is done by circuitry that includes an adaptive filter.

5. A method according to claim 4, further comprising:

comparing the amplitude of the signal from the first microphone and the amplitude of the signal from the second microphone with a threshold; and in the event that the amplitude of the signal from either or both of the first microphone or second microphone is less that a threshold, inhibiting update of the coefficients of the adaptive filter.

6. A method according to claim 4, further comprising:

determining a ratio of the amplitude of the signal from the first microphone to the amplitude of the signal from the second microphone; and in the event that the ratio of the amplitude of the signal from the first microphone to the amplitude of the signal from the second microphone is greater than a threshold ratio, inhibiting update of the coefficients of the adaptive filter.

7. A method according to claim 1, further comprising smoothing the signal from the first microphone and the second microphone.

8. A method according to claim 7, wherein the smoothing comprises low pass filtering.

9. An engine harmonic cancellation system comprising:

at least two microphones;

detecting circuitry for detecting the presence of noise that affects the reading of a first of the plurality of microphones differently that the noise affects the reading of a second of the plurality of microphones, comprising correlation determining circuitry to determine if a signal from the first microphone is correlated with a signal from a second microphone; and comparing circuitry for determining if the amount of noise exceeds a threshold, the correlation determining circuitry comprising:

an adaptive filter, providing, based on the signal from the first microphone, a predicted signal from the second microphone; and the comparing circuitry comparing the amplitude of the predicted signal from the second microphone with the amplitude of the signal from the second microphone.

10. An engine harmonic cancellation system according to claim 9, the determining circuitry further comprising:

circuitry updating coefficients of the adaptive filter;

circuitry comparing the amplitude of the signal from the first microphone and the signal of the second microphone with a threshold; and circuitry inhibiting update of coefficients of the adaptive filter if either or both the amplitude of the signal from the first microphone and the amplitude of the signal from the second microphone are less than the threshold.

11. An engine harmonic cancellation system according to claim 9, the determining circuitry further comprising:

circuitry updating coefficients of the adaptive filter;

circuitry comparing the ratio of the amplitude of the signal from the first microphone to the amplitude of the signal from the second microphone with a threshold; and circuitry inhibiting update of coefficients of the adaptive filter if the ratio of the amplitude of the signal from the first microphone to the amplitude of the signal from the second microphone is greater than the threshold.

12. An engine harmonic cancellation system according to claim 9, further smoothing circuitry, smoothing the signal from the first microphone and the signal from the second microphone.

13. An engine harmonic cancellation system according to claim 12, wherein the smoothing circuitry comprises a low pass filter.

* * * * *